United States Patent

Schade et al.

Patent Number: 6,015,551
Date of Patent: Jan. 18, 2000

[54] COPOLYMERS OF CARBOXYLIC ACIDS AND MULTIPLY OLEFINICALLY UNSATURATED CARBOXYLIC ACID DERIVATIVES AND THEIR USE AS THICKENERS AND DISPERGENTS

[75] Inventors: Christian Schade, Ludwigshafen; Hans-Ulrich Wekel, Ellerstadt; Axel Sanner, Frankenthal; Karin Sperling, Neustadt, all of Germany

[73] Assignee: BASF Aktiengesellschaft, Ludwigshafen, Germany

[21] Appl. No.: 09/077,598

[22] PCT Filed: Dec. 11, 1996

[86] PCT No.: PCT/EP96/05522

§ 371 Date: Jun. 2, 1998

§ 102(e) Date: Jun. 2, 1998

[87] PCT Pub. No.: WO97/21744

PCT Pub. Date: Jun. 19, 1997

[30] Foreign Application Priority Data

Dec. 14, 1995 [DE] Germany ............ 195 46 698

[51] Int. Cl.[7] .......... A61K 31/74; C08L 67/00; C08G 63/00
[52] U.S. Cl. ........ 424/78.08; 528/271; 528/272; 528/274; 528/302; 528/303; 528/305; 528/306; 524/599; 524/601; 523/500; 522/1; 522/6; 424/78.12; 424/78.2; 424/78.33
[58] Field of Search ................... 528/271, 272, 528/274, 302, 303, 305, 306; 524/599, 601; 523/500; 522/1, 6; 424/78.08, 78.18, 78.2, 78.33

[56] References Cited

FOREIGN PATENT DOCUMENTS

| 328 725 | 8/1989 | European Pat. Off. . |
|---|---|---|
| 335 624 | 10/1989 | European Pat. Off. . |
| 435 066 | 7/1991 | European Pat. Off. . |
| 93/22357 | 11/1993 | WIPO . |

*Primary Examiner*—Samuel A. Acquah
*Attorney, Agent, or Firm*—Keil & Weinkauf

[57] ABSTRACT

The disclosure relates to a copolymer obtainable by radically initiated polymerization of the following: A) 70–99.9 wt. % an olefinically unsaturated $C_3$–$C_5$ monocarboxylic acid, an olefinically unsaturated $C_4$–$C_8$ dicarboxylic acid or its anhydride, or a mixture of such carboxylic acids; with B) 0.1–30 wt. % one or more multiply olefinically unsaturated carboxylic acid derivatives of formula (I)

$$Z—Y—(CHR^3—CH_2—X)_n—R^4 \qquad (I)$$

in which Z is a vinyl or allyl group or structure (a),

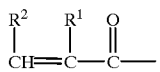

$R^1$, $R^2$ are hydrogen or methyl, $R^3$ is hydrogen, methyl or ethyl, $R^4$ is a singly or multiply olefinically unsaturated alkenyl or cycloalkenyl group or a singly or doubly olefinically unsaturated arylalkylene group, X is oxygen or NH, Y is oxygen, NH or N-alkyl, n is a number between 0 and 50; and C) 0–29.9 wt. % other copolymerizable monomers. The proposed copolymer can be used as a thickener or dispergent for aqueous systems.

7 Claims, No Drawings

COPOLYMERS OF CARBOXYLIC ACIDS AND MULTIPLY OLEFINICALLY UNSATURATED CARBOXYLIC ACID DERIVATIVES AND THEIR USE AS THICKENERS AND DISPERGENTS

The present invention relates to novel copolymers of carboxylic acids and polyolefinically unsaturated derivatives of the general formula I, with or without one or more copolymerizable monomers. The present invention furthermore relates to the use of these copolymers as thickeners or dispersants, in particular in cosmetic preparations, and to pharmaceutical and, in particular, cosmetic preparations comprising these copolymers.

Conventionally employed as thickeners or viscosity regulators are copolymers of olefinically unsaturated carboxylic acids such as (meth)acrylic acid, maleic acid or maleic anhydride, hydrophobic comonomers such as esters of (meth)acrylic acid and small amounts of a crosslinker, ie. a compound with at least two olefinically unsaturated groups in the molecule. Copolymers of these types are described, for example, in EP-A 328 725 and EP-A 435 066.

In order to achieve an adequate thickening effect, it is necessary for crosslinking to take place during the polymerization. However, control of the crosslinking entails problems with the crosslinker components conventionally employed, for example divinylbenzene, pentaerythritol triallyl ether, diallyltartaramide, bisacrylamidoacetic acid, methylenebisacrylamide, allyl methacrylate, trimethylolpropane diallyl ether or allyl ethers of sucrose. Because of the high double-bond density, many of these compounds are very reactive and therefore form an additional safety risk, and are difficult to store and have an increased skin-irritant potential. In addition, this makes the crosslinking generally take place in a very heterogeneous fashion so that the polymers still contain relatively large amounts of uncrosslinked portions. Because of the high reactivity of the crosslinkers, in general only small amounts of the crosslinking component are used, and even small variations in the crosslinker concentration, as occur in production processes, therefore lead to marked variations in the thickening effect of the copolymers.

It is an object of the present invention to provide a polymer which can be employed as thickener or dispersant and whose thickening effect can be controlled better.

We have found that this object is achieved by a copolymer which is obtainable by free-radical polymerization of A) 70–99.9% by weight of an olefinically unsaturated $C_3$–$C_5$-monocarboxylic acid, of an olefinically unsaturated $C_4$–$C_8$-dicarboxylic acid or of its anhydride or of a mixture of such carboxylic acids or carboxylic anhydrides with B) 0.1–30% by weight of one or more polyolefinically unsaturated derivatives of the general formula I (I)

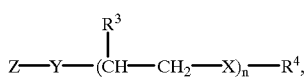

where

Z is a vinyl or allyl group or the structure

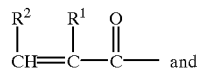

$R^1$, $R^2$ are identical or different and are hydrogen or methyl, $R^3$ is hydrogen, methyl or ethyl, $R^4$ is a mono- or polyolefinically unsaturated $C_6$–$C_{30}$-alkenyl or -cycloalkenyl radical with 5 to 8 carbon atoms in the ring or a mono- or diolefinically unsaturated arylalkenyl radical with a total of 9 to 15 carbon atoms, X is oxygen or NH, Y is oxygen, NH or N-alkyl, n is a number from 0 to 50, and C) 0–29.9% by weight of one or more copolymerizable monomers.

In a preferred embodiment, the copolymer according to the invention is composed of A) 80–99.5% by weight, in particular 90–99% by weight, of the carboxylic acid component A, B) 0.5–20% by weight, in particular 1–10% by weight, of the polyolefinically unsaturated derivative I and C) 0–19.5% by weight, in particular 0–9% by weight, of one or more copolymerizable monomers.

Particularly suitable as component A are acrylic acid, methacrylic acid or maleic anhydride, but also, in addition, crotonic acid, 2-pentenoic acid, maleic acid, fumaric acid or itaconic acid.

The radical $R^1$ in the derivatives I is hydrogen or methyl.
The radical $R^2$ in the derivatives I is preferably hydrogen.
The radical $R^3$ in the derivatives I is hydrogen, methyl or ethyl, preferably hydrogen or methyl.

The variable X in the derivatives I is preferably oxygen.

The variable Y in the derivatives I is oxygen, NH or N-alkyl. Suitable and preferred as N-alkyl radicals are $C_1$–$C_4$-alkyl radicals such as methyl, ethyl, propyl, i-propyl, butyl, i-butyl and t-butyl. Y is particularly preferably oxygen and NH, very particularly preferably oxygen.

The degree of alkoxylation or alkimination n is preferably 0 to 20, in particular 0 to 7, very particularly preferably 0 or 1.

The radical $R^4$ in the derivatives I is a mono- or polyolefinically unsaturated $C_6$–$C_{30}$-alkenyl or -cycloalkenyl radical with 5 to 8 carbon atoms in the ring or a mono- or diolefinically unsaturated arylalkyl radical, preferably phenylalkenyl or naphthylalkenyl radical with a total of 9 to 15 carbon atoms.

Examples of the radical $R^4$ are the long-chain or sterically demanding radicals of the following unsaturated alcohols: 2-hexen-1-ol, 5-hexen-1-ol, 3-hexen-1-ol, 1-octen-3-ol, 9-decen-1-ol, 13-tetradecen-1-ol, citronellol, nerol, linalool, terpineol, nopol, farnesol, linolyl alcohol, linolenyl alcohol, 13-docosenol, 12-hydroxy-9-octadecenol, palmitoleyl alcohol, oleyl alcohol, 3-phenyl-2-propenol (cinnamyl alcohol) or 5-phenyl-2,4-pentadienol. Of these, the oleyl radical is particularly preferred.

Very particularly preferred as component B are polyolefinically unsaturated carboxylic acid derivatives of the general formula Ia

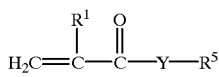

(Ia)

where $R^1$ and Y have the abovementioned meanings, and $R^5$ is a mono- to triolefinically unsaturated $C_8$–$C_{18}$-alkenyl or -cycloalkenyl radical with 5 to 8 carbon atoms in the ring or a mono- or diolefinically unsaturated phenylalkenyl radical with a total of 9 to 12 carbon atoms.

The derivatives I and the carboxylic acid derivatives Ia are easily obtainable by known preparation processes, for example by esterification of (meth)acrylic acid with alcohols of the formula $R^4/R^5$—OH or ethoxylated, propoxylated or butoxylated alcohols of the formula $R^4/R^5$—(O—$CH_2$–$CHR^2)_n$—OH or by reaction of reactive (meth)acrylic acid derivatives with amines of the formula $R^4/R^5$—$NH_2$ and their ethoxylated, propoxylated or butoxylated derivatives.

It is also possible to employ in place of the (meth)acrylic esters the appropriate allyl ethers, vinyl ethers or vinyl esters. Products of the reaction of reactive monomers such as glycidyl (meth)acrylate or (meth)allyl isocyanate with the alcohols and amines described likewise afford suitable comonomers B. 1-eicosene, 1-tetracosene, $C_1$–$C_{18}$ vinyl esters such as vinyl acetate, vinyl propionate or vinyl versatate, (meth)acrylic esters of ethylene glycol, diethylene glycol or their higher homologs, and the monoalkyl ethers derived therefrom, eg. diethylene glycol monoethyl ether. It is also, of course, possible to employ mixtures of said monomers C. Particularly preferred monomers C are $C_8$–$C_{24}$-alkyl (meth)acrylates and $C_8$–$C_{30}$-alkenes.

In special cases, small amounts of a polyethylenically unsaturated compound can be added to the reaction mixture to assist crosslinking.

The copolymers according to the invention can be prepared by free-radical polymerization of monomers A to C in principle by all known processes. A particularly suitable preparation method is precipitation polymerization, in which the monomers, but not the polymer, are soluble in the solvent system employed.

Examples of suitable solvents are aromatic and saturated aliphatic hydrocarbons. Examples of aromatic hydrocarbons are benzene, toluene, xylene and isopropylbenzene. The saturated aliphatic hydrocarbons preferably have 5 to 12 carbon atoms. Pentane, n-hexane, cyclohexane, heptane, octane and isooctane are suitable. The precipitation polymerization can also be carried out in halogenated saturated aliphatic hydrocarbons such as 1,1,1-trichloroethane or methylene chloride. Also suitable as reaction medium are ethers, $C_2$–$C_6$-alkyl esters of formic acid or of acetic acid, ketones with 3 to 6 carbon atoms, liquid or supercritical carbon dioxide, ethane, propane or butane. Examples of suitable ethers are tert-butyl methyl ether or isobutyl methyl ether. The alkyl esters of formic acid or acetic acid are preferably derived from saturated alcohols with 2 to 6 carbon atoms, eg. ethyl formate, methyl acetate, ethyl acetate, (iso)propyl acetate or (iso)butyl acetate. Examples of suitable ketones are acetone and methyl ethyl ketone. The diluents can be employed alone or mixed with one another. Preferably employed as diluents in the precipitation polymerization are saturated aliphatic hydrocarbons which have 5 to 8 carbon atoms in the molecule and which can be straight-chain or branched, cyclic or bicyclic, alkyl esters of acetic acid, methylene chloride or supercritical carbon dioxide. Cyclohexane is particularly preferably employed as solvent in the precipitation polymerization. The amount of solvent is advantageously chosen so that the reaction mixture can be stirred during the polymerization. The solids content of the mixture after the polymerization is preferably in the range from 10 to 40% by weight.

The molecular weight of the copolymers can, if required, be reduced by adding regulators to the polymerizing mixture. Examples of suitable regulators are mercapto compounds such as dodecyl mercaptan, thioethanol, thioglycolic acid or mercaptopropionic acid. If regulators are present, they are used in amounts of from 0.1 to 5% of the weight of the monomers employed.

The copolymerization takes place in the presence of polymerization initiators which form free radicals. Suitable compounds of this type are azo or peroxo compounds, eg. diacyl peroxides such as dilauroyl peroxide, didecanoyl peroxide and dioctanoyl peroxide or peresters such as tert-butyl peroctanoate, tert-butyl perpivalate, tert-amyl perpivalate or tert-butyl perneodecanoate, and azo compounds such as dimethyl 2,2'-azobis(isobutyrate), 2,2'-azobis (isobutyronitrile), 2,2'-azobis(2-methylbutyronitrile) or 2,2'-azobis(2,4-dimethylvaleronitrile). The initiators are employed in the amounts customary in precipitation polymerizations, e(. in amounts of from 0.05 to 5% of the weight of the monomers. It is possible to add to the polymerization mixture water, alcohols, protective colloids, emulsifiers in a small amount, or else larger amounts of a base, eg. potassium carbonate. If water and/or bases are present during the precipitation polymerization, then they are so only in amounts such that the mixture of all the components still appears homogeneous before the polymerization starts.

The precipitation polymerization is normally carried out under an inert gas atmosphere. The copolymerization can be carried out, for example, in such a way that all the components present during the polymerization are introduced into a polymerization vessel, the reaction is started, and the reaction mixture is cooled if necessary in order to control the polymerization temperature. However, the procedure may also be such that only a part of the components to be polymerized is introduced, the polymerization is started, and the remainder of the mixture to be polymerized is metered in continuously or in portions, depending on the progress of the polymerization. However, the process can also be such that initially the diluent is introduced together with a surfactant, and the monomers and the polymerization initiator are introduced into this separately and continuously or in portions.

In order to achieve permanent thickening of water and aqueous systems and/or stabilization of oil-in-water emulsions, the dispersed polymer is adequately neutralized with a base. Examples of suitable bases are alkali metal bases such as alkali metal hydroxides, bicarbonates and carbonates, for example NaOH, KOH and sodium and potassium carbonates, ammonia and organic amines, pyridines and amidines or mixtures thereof. Preferably used on neutralization with organic amines are alkanolamines from the series of mono-, di- or trialkanolamines with 2 to 5 carbon atoms in the alkanol residue such as mono-, di- or triethanolamine, mono-, di- or tri(iso)propanolamine or 2-amino-2-methylpropanol, alkanediolamines with 2 to 4 carbon atoms in the alkanediol residue such as 2-amino-2-methyl-1,3-propanediol or 2-amino-2-ethyl-1,3-propanediol, alkanepolyolamines such as tetrahydroxypropylethylenediamine, tris(hydroxymethyl) aminomethane or N,N,N',N'-tetrakis(2-hydroxypropyl) ethylenediamine, alkylamines such as di(2-ethylhexyl)

amine, triamylamine or dodecylamine and amino ethers such as morpholine.

The cosmetic or pharmaceutical preparations may moreover contain as oil all the oils which can customarily be used for this purpose. The total amount of the oil phase in the emulsion can moreover be up to 80% by weight. The content of the oil phase in the cosmetic or pharmaceutical preparations is preferably from 10 to 50% by weight. The slightly crosslinked copolymers are preferably used for stabilization in creams or lotions. In addition they are also very suitable for thickening aqueous systems or forming thickened gels after the dispersed copolymer has been adequately neutralized by addition of a base.

In contrast to slightly crosslinked homopolymers of acrylic acid it is possible with the copolymers to be used according to the invention to stabilize oil-in-water emulsions permanently. The amounts of crosslinked copolymers prepared by precipitation polymerization which are preferably employed are from 0.05 to 2% of the weight of the emulsions.

The use of the polyolefinically unsaturated derivatives I, which simultaneously contain a hydrophobic moiety which is necessary for modifying the carboxylic acids A, and several olefinically unsaturated groups to achieve the crosslinker properties, have made the use of the crosslinker components which are otherwise customary and whose problems have been described at the outset substantially unnecessary.

EXAMPLES

Unless otherwise indicated, the percentage data relate to weight. The viscosity was, unless described otherwise, measured with a manual viscometer (Hake VT-02) at 23° C.

Example 1

1400 ml of 1,1,1-trichloroethane, 250 g of acrylic acid and 10 g of oleyl methacrylate were stirred in a 3 l flat flange flask and flushed with nitrogen for 30 min. The mixture was heated to 80° C. with stirring under a stream of nitrogen, arid after reaching this temperature over 3 h 100 ml of 1,1,1-trichloroethane and 0.4 g of dilauroyl peroxide were metered in. After a further 3 h, the mixture was cooled, and the precipitated product was filtered off, washed with 500 ml of 1,1,1-trichloroethane and dried at 60° C. under reduced pressure.

To determine the gel viscosity, 1.0 g of the polymer was dispersed in 190 ml of water in a beaker. 10 ml of a 10% strength triethanolamine solution were added with stirring. The viscosity of the resulting gel was determined with a manual viscometer (Hake VT-02) as 10.0 Pa.s at 23 C. It was evident when the gel was spread on a glass plate that it was smooth and virtually free of specks.

To check the emulsifiability, 0.4 g of the polymer was weighed into a beaker and dispersed in 30 ml of liquid paraffin. Then 100 ml of water arid subsequently 4 ml of a 10% strength triethanolamine solution were added with vigorous stirring. The emulsion was homogenized with a dispersing unit at 8000 rpm for a few seconds. The viscosity was determined as above to be 7.5 Pa.s. The texture of the emulsion was assessed after 1 h by spreading on a glass plate. To determine the long-term stability, a 100 ml graduated cylinder was filled with the emulsion, which was assessed after 14 days. At this time, the emulsion showed no tendency to separate.

Example 2

1320 ml of cyclohexane, 50 g of acrylic acid, 1 g of oleyl allyl ether and 80 mg of 2,2'-azobis(2-methylbutyronitrile) were introduced into a flask which had a capacity of 3000 ml and was equipped with a stirrer and an apparatus for working under protective gas and were heated to 80° C. while stirring under a stream of nitrogen. After this temperature was reached, 200 g of acrylic acid and 4 g of oleyl allyl ether were fed in dropwise over the course of 2 hours, and 80 ml of cyclohexane and 320 mg of 2,2'-azobis(2-methylbutyronitrile) were fed in dropwise over the course of 3 hours. After addition of the polymerization initiator was complete, the reaction mixture was stirred at 80 ° C. for 3 hours. The product was then filtered off with suction and dried at 50° C. under reduced pressure. 251 g of a white polymer powder with a gel viscosity of 7.5 Pa.s were obtained.

Examples 3 to 7

Examples 3 to 7 were carried out in a similar way using various amounts of comonomer B and the same amounts of acrylic acid, solvent and initiator. Table I shows the results.

TABLE I

Composition and viscosities of the copolymers from Examples 3 to 7

| Example No. | Comonomer B | Solvent [Ratio by vol.] | Viscosity [Pa · s] Gel | Emulsion |
|---|---|---|---|---|
| 3 | 5 g oleyl methacrylate | cyclohexane | 26 | 19.0 |
| 4 | 5 g oleyl acrylate | ethyl acetate/ cyclohexane (1:1) | 17 | 9.0 |
| 5 | 3.5 g oleyl methacrylate 3.5 g stearyl methacrylate | cyclohexane | 12 | 8.0 |
| 6 | 2.5 g oleyl methacrylate 2.5 g stearyl methacrylate 2.5 g 1-octadecene | cyclohexane | 8 | 6.5 |
| 7 | 2.5 g oleyl methacrylate | isopropyl acetate | 12 | 9.0 |

Examples 8 (Comparative Example) and 9

Examples 8 and 9 were carried out in a similar way to Example 1 using various amounts of comonomer B and various amounts of pentaerythritol triallyl ether as comparative crosslinker and the same amount of acrylic acid, cyclohexane as solvent and initiator. Table II shows the results.

Table II

Test comparing standard crosslinker pentaerythritol triallyl ether and oleyl methacrylate

| Example | Crosslinker | Viscosity [Pa · s] Gel | Emulsion |
|---|---|---|---|
| 8 a) | 1 g pentaerythritol triallyl ether | 8 | 6 |
| b) | 1.5 g pentaerythritol triallyl ether | 14 | 9 |
| c) | 2 g pentaerythritol triallyl ether | 22 | 16.5 |
| d) | 3 g pentaerythritol triallyl ether | 13 | 7.5 |
| 9 a) | 3.75 g oleyl methacrylate | 17 | 10 |
| b) | 6.25 g oleyl methacrylate | 27 | 19.5 |
| c) | 7.5 g oleyl methacrylate | 23 | 17 |
| d) | 8.75 g oleyl methacrylate | 17 | 10.5 |

The results show that the gel and emulsion viscosity reacts less sensitively to the crosslinker concentration (see gram data in Table II) on use of oleyl methacrylate than on use of pentaerythritol triallyl ether.

We claim:

1. A copolymer obtained by free-radical polymerization of
   A) 70–99.9% by weight of an olefinically unsaturated $C_3$–$C_5$-monocarboxylic acid, of an olefinically unsaturated $C_4$–$C_8$-dicarboxylic acid or of its anhydride or of a mixture of such carboxylic acids or carboxylic anhydrides with
   B) 0.1–30% by weight of one or more polyolefinically unsaturated derivatives of the general formula

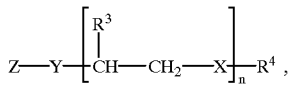 (I)

where
   Z is a vinyl or allyl group or the structure

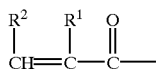

and
   $R^1$, $R^2$ are identical or different and are hydrogen or methyl,
   $R^3$ is hydrogen, methyl or ethyl,
   $R^4$ is a mono- or polyolefinically unsaturated $C_6$–$C_{30}$-alkenyl or -cycloalkenyl radical with 5 to 8 carbon atoms in the ring or a mono- or diolefinically unsaturated arylalkenyl radical with a total of 9 to 15 carbon atoms,
   X is oxygen or NH,
   Y is oxygen, NH or N-alkyl,
   n is 0 or 1, and
   C) 0–29.9% by weight of one or more copolymerizable monomers.

2. A copolymer as claimed in claim 1, obtained by free-radical polymerization of
   A) 80–99.5% by weight of the carboxylic acid component A,
   B) 0.5–20% by weight of the polyolefinically unsaturated carboxylic acid derivative I and
   C) 0–19.5% by weight of one or more copolymerizable monomers.

3. A copolymer as claimed in claim 1, wherein component A is acrylic acid, methacrylic acid or maleic anhydride.

4. A copolymer as claimed in claim 1, wherein component B is one or more polyolefinically unsaturated carboxylic acid derivatives of the general formula Ia

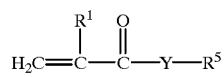 Ia where $R^1$ is hydrogen or methyl, Y is oxygen, NH or N-alkyl and $R^5$ is a mono- to triolefinically unsaturated $C_8$–$C_{18}$-alkenyl or -cycloalkenyl radical with 5 to 8 carbon atoms in the ring or a mono- or diolefinically unsaturated phenylalkenyl radical with a total of 9 to 12 carbon atoms.

5. A process for preparing the copolymers as claimed in claim 1, which comprises free-radical polymerization of the monomers.

6. A cosmetic or pharmaceutical preparation comprising copolymers as claimed in claim 1 as thickeners or dispersants in amounts of from 0.01 to 5% by weight, based on the emulsion.

7. An aqueous composition comprising, as a thickener or dispersant, an effective amount of a copolymer as defined in claim 1.

* * * * *